United States Patent [19]

Schaar

[11] 4,211,226
[45] Jul. 8, 1980

[54] DISPOSABLE DIAPER WITH FLAP COVERED TAPE FASTENER

[75] Inventor: Charles H. Schaar, Lake Zurich, Ill.

[73] Assignee: Colgate-Palmolive Company, New York, N.Y.

[21] Appl. No.: 30,493

[22] Filed: Apr. 16, 1979

Related U.S. Application Data

[63] Continuation of Ser. No. 745,273, Nov. 26, 1976, abandoned.

[51] Int. Cl.³ ............................................. A61F 13/16
[52] U.S. Cl. .............................. 128/287; 128/DIG. 30
[58] Field of Search ................. 128/284, 287, DIG. 30

[56] References Cited

U.S. PATENT DOCUMENTS

| 3,103,930 | 9/1963 | Collett et al. | 128/DIG. 30 |
| 3,554,195 | 1/1971 | Murdoch | 128/284 |
| 3,840,013 | 1/1974 | Mesek et al. | 128/287 |
| 3,901,237 | 8/1975 | Cepuritis | 128/284 |
| 3,901,239 | 8/1975 | Tritsch | 128/287 |
| 3,921,639 | 11/1975 | Cepuritis | 128/DIG. 30 |
| 3,955,576 | 5/1976 | Safford | 128/287 |
| 3,971,380 | 7/1976 | Tritsch | 128/287 |
| 3,978,861 | 9/1976 | Schaar | 128/287 |
| 4,122,552 | 10/1978 | Tedford | 128/DIG. 30 |

FOREIGN PATENT DOCUMENTS 987451 of 1976 Canada ............................ 128/DIG. 30

Primary Examiner—William E. Kamm
Assistant Examiner—C. W. Shedd
Attorney, Agent, or Firm—Powell L. Sprunger

[57] ABSTRACT

A disposable diaper comprising, an absorbent pad assembly having an absorbent pad, and a sheet covering a surface of the pad. The sheet has a slit defining a strip connected to the remaining portion of the sheet. The diaper has a pressure-sensitive tape strip secured to the pad assembly and extending across an opening defined by the slit, with the tape strip having adhesive facing toward the sheet strip. The sheet strip is releasably attached to the adhesive and is peeled from the tape strip in order to expose the adhesive through the opening for use in securing the diaper about an infant.

4 Claims, 8 Drawing Figures

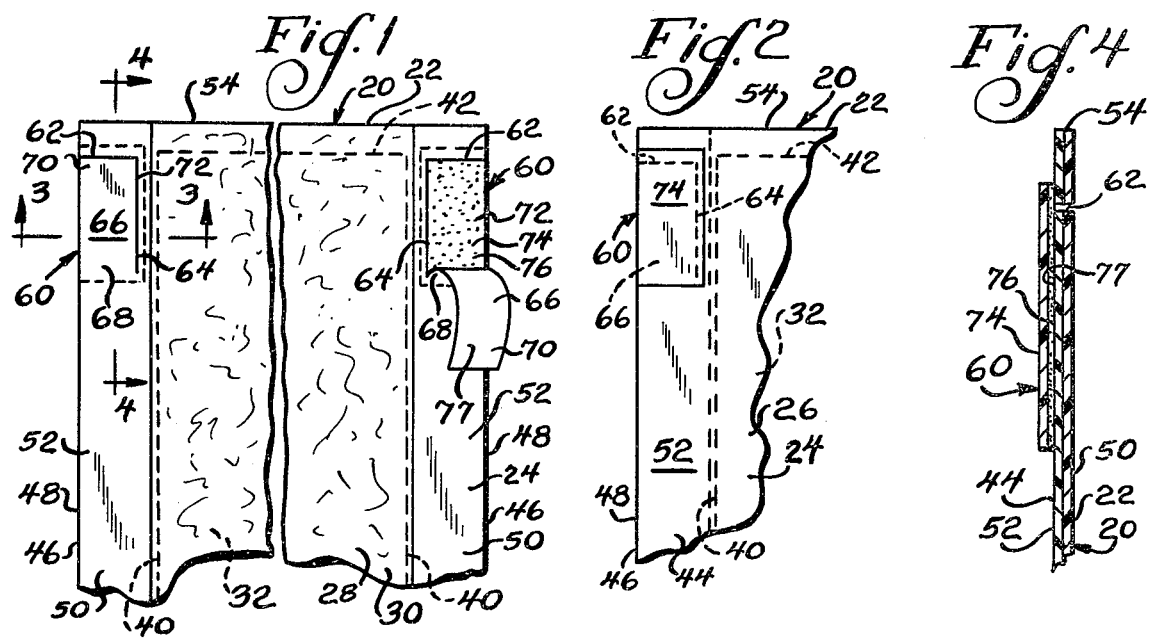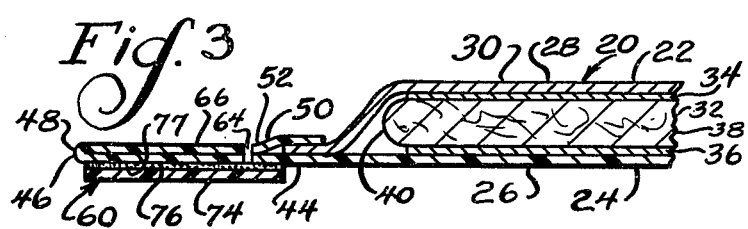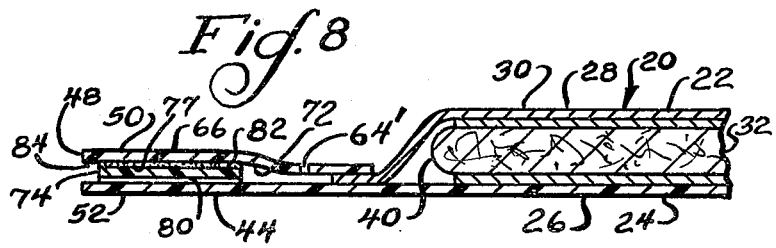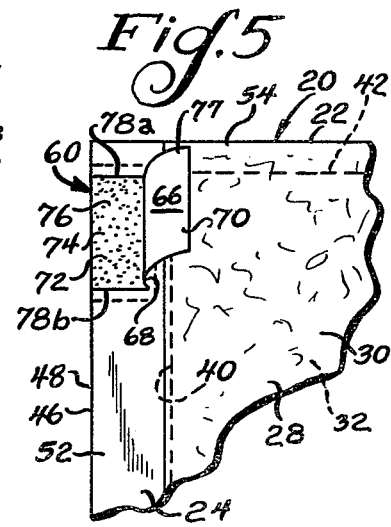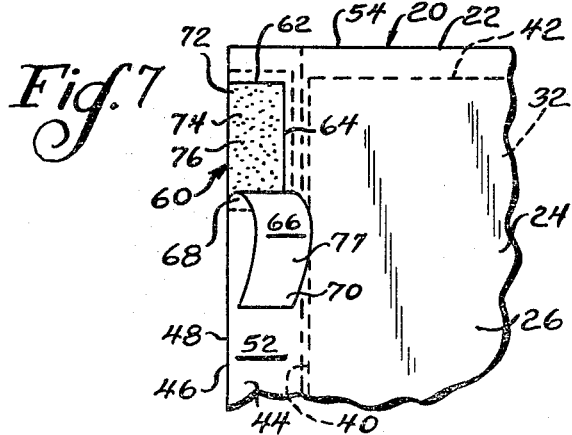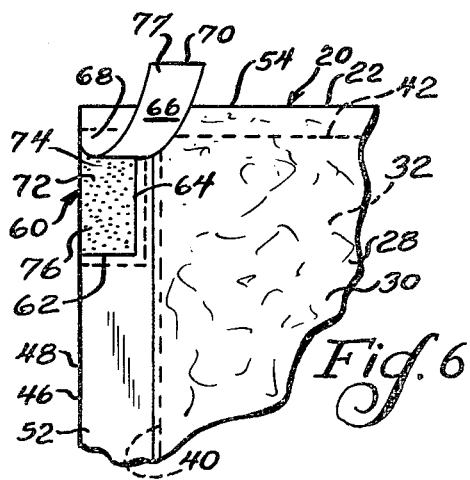

DISPOSABLE DIAPER WITH FLAP COVERED TAPE FASTENER

This is a continuation, of application Ser. No. 745,273 filed Nov. 26, 1976, now abandoned.

BACKGROUND OF THE INVENTION

The present invention relates to absorbent articles, and more particularly to disposable diapers.

A various assortment of disposable diapers have been proposed for use on infants, and have become increasingly popular since they may be disposed after a single use and need not be laundered. The diapers are normally constructed from a fluid impervious backing sheet, a top or cover sheet, and an absorbent pad located intermediate the backing and cover sheets. Tape fasteners have also been proposed for the diapers, and are utilized to secure the diaper about an infant during placement. Such tape fasteners normally comprise a pressure-sensitive adhesive tape, and a release sheet covering adhesive on the tape strip. The release sheet is removed during placement of the diaper, in order to expose adhesive on the tape strip for attaching the diaper about the infant. The prior tape fasteners have required a separate release sheet in order to cover the adhesive, which adds to the expense of manufacture and the ultimate cost to the consumer. Additionally, it is desirable to eliminate the inconvenience of discarding separate release sheets during placement of the diaper.

SUMMARY OF THE INVENTION

A principal feature of the present invention is the provision of a disposable diaper having an improved tape fastener.

The diaper of the present invention comprises, an absorbent pad assembly having an absorbent pad, and a sheet covering a surface of the pad. The sheet has a slit defining a strip connected to the remaining portion of the sheet. The diaper has a pressure-sensitive tape strip secured to the pad assembly and extending across an opening defined by the slit, with the tape strip having adhesive facing toward the sheet strip, and with the sheet strip being releasably attached to the adhesive on the tape strip.

A feature of the present invention is that the sheet strip may be peeled from the tape strip in order to expose the adhesive on the tape strip through the opening for use in securing the diaper about an infant.

Another feature of the invention is that the sheet strip comprises an integral part of the diaper and eliminates the cost of separate release sheets for the tape strips.

Thus, a feature of the present invention is that the diaper may be constructed at a reduced cost for the consumer.

Still another feature of the invention is that the tape fastener eliminates the necessity for discarding separate release sheets during placement of the diaper.

A feature of the invention is that the tape fastener may be prepared for use in securing the diaper about an infant in a simplified manner.

Further features will become more fully apparent in the following description of the embodiments of this invention and from the appended claims.

DESCRIPTION OF THE DRAWINGS

In the drawings:

FIG. 1 is a fragmentary front plan view of a disposable diaper having a tape fastener of the present invention;

FIG. 2 is a fragmentary back plan view of the diaper of FIG. 1;

FIG. 3 is a fragmentary sectional view taken substantially as indicated along the line 3—3 of FIG. 1;

FIG. 4 is a fragmentary sectional view taken substantially as indicated along the line 4—4 of FIG. 1;

FIG. 5 is a fragmentary front plan view of another embodiment of the diaper of the present invention;

FIG. 6 is a fragmentary front plan view of another embodiment of a disposable diaper of the present invention;

FIG. 7 is a fragmentary back plan view of another embodiment of a disposable diaper of the present invention; and FIG. 8 is a fragmentary sectional view of another embodiment of a disposable diaper of the present invention.

DESCRIPTION OF THE PREFERRED EMBODIMENTS

Referring now to FIGS. 1-4, there is shown a disposable diaper generally designated 20 having an absorbent pad assembly 22. The pad assembly 22 has a fluid impervious thermoplastic backing sheet 24, such as polyethylene, defining a back surface 26 of the pad assembly, a fluid pervious cover or top sheet 28 defining a substantial part of a front surface 30 of the pad assembly 22, and an absorbent pad 32 located between the backing sheet 24 and top sheet 28. The pad 32 may have a front wadding sheet 34, a back wadding sheet 36, and a pad portion 38, such as comminuted wood pulp termed in the art as fluff, located between the front and back wadding sheets 34 and 36 which serve to increase the structural integrity of the pad portion 38. The absorbent pad 32 has a pair of side edges 40, and a pair of end edges 42 connecting the side edges 40. The backing sheet 24 has a pair of first side sections 44 extending past the opposed side edges 40 of the pad 32, a pair of fold lines 46 defining opposed side edges 48 of the pad assembly 22, and a pair of second side sections 50 extending inwardly from the respective fold lines 46. Thus, the doubled portion of the first and second side sections 44 and 50 define opposed side margins 52 of the pad assembly 22, and the first and second sections 44 and 50 of the side margins 52 may be fused together longitudinally along the pad assembly 22. The pad assembly 22 has a pair of end edges 54 connecting the side edges 48, and may have a plurality of longitudinally extending fold lines defining a box-pleat configuration of the pad assembly.

The diaper 20 has a pair of tape fasteners generally designated 60 adjacent opposed side edges 48 of the pad assembly and adjacent an end edge 54 of the pad assembly. As shown, each of the side margins 52 of the backing sheet 24 has a first slit 62 extending from the respective side edge 48 of the pad assembly 22 inwardly toward a lateral central portion of the diaper, and a second slit 64 extending from an inner portion of the first slit 62 in a direction away from the adjacent end edge 54 of the pad assembly 22. Thus, the first and second slits 62 and 64, with a portion of fold line 46, define a covering strip 66 of the doubled portion of the backing sheet 24 in each side margin 52. The covering strips 66 are connected at one end 68 to the remaining portion of the backing sheet 24, and their free ends 70 define respective openings 72 in the diaper side margins 52.

The diaper 20 also has a pair of pressure-sensitive tape strips 74 secured to the back surface 26 of the pad assembly 22 at a location with the tape strips 74 extending across the respective openings 72 defined by the slits in the pad assembly side margins 52. As shown, the tape strips 74 have adhesive 76 on a surface facing toward the sheet covering strips 66. In the packaged configuration of a diaper, the covering strips 66 are releasably attached to the adhesive 76 on the tape strips 74, as shown in the left-hand portion of FIG. 1, with the heat-treated surface of the covering strips 66 serving as a release surface 77 to facilitate removal of the covering strips 66 from the adhesive 76. During placement of the diaper, the free ends 70 of the covering strips 66 may be peeled from the adhesive 76 on the tape strips 74 in order to expose the adhesive 76 through the openings 72 in the diaper side margins 52, as illustrated in the right-hand portion of FIG. 1, and the exposed adhesive 76 may be utilized to secure the diaper about the infant.

In this manner, the covering strips 66 may be readily removed from the tape strips 74 in order to expose adhesive for placement of the diaper about an infant. At the same time, the covering strips 66 are an integral portion of the diaper 20 itself, and remain attached to the diaper after removal of the tape strip adhesive 76 in order to eliminate the necessity for discarding separate release sheets during placement of the diaper. In fact, the diaper of the present invention eliminates separate release sheets altogether, thus reducing the expense of diaper materials and the cost to the consumer.

Another embodiment of the present invention is illustrated in FIG. 5, in which like reference numerals designate like parts. In this embodiment, the covering strip 66 is defined by a pair of spaced slits 78a and 78b which extend inwardly from the side edge 48 of the pad assembly 22 toward a lateral central portion of the diaper. Thus, the covering strips 66 of the pad assembly side margins 52 are defined by the fold line 46 and the slits 78a and b, with the covering strips 66 being connected at inner ends 68 to the remaining portion of the backing sheet 24 in the side margins 52. The tape strips 74 are secured to the back surface of the pad assembly across the openings 72 in the diaper side margins 52, and the connected covering strips 66 are peeled from the adhesive 76 of the tape strips 74 inwardly in order to expose the adhesive for securing the diaper about an infant.

Another embodiment of the present invention is illustrated in FIG. 6, in which like reference numerals designate like parts. In this embodiment, the tape fastener 60 is similar to the fastener described in connection with FIGS. 1-4, with the exception that the second slit 64 extends from an inner portion of the first slit 62 in a direction toward the adjacent end edge 54 of the pad assembly. The covering strips 66 are peeled from the adhesive 76 of the tape strips 74 in a direction toward the adjacent end edge 54 of the pad assembly. In this manner, the adhesive 76 is exposed for securing the diaper about an infant while the covering strips 66 of the backing sheet 24 remain connected to the diaper.

Another embodiment of the present invention is illustrated in FIG. 7, in which like reference numerals designate like parts. In this embodiment, the tape fastener 60 is similar to the fastener described in connection with FIGS. 1-4, except that the tape strips 74 are secured to the front surface of the diaper side margins 52. Thus, the covering strips 66 of the pad assembly side margins 52 are peeled from the adhesive 76 on the tape strips 74, such that the adhesive 76 faces through the openings 72 toward the back surface 26 of the pad assembly 22 for use in securing the diaper about the infant. As before, the covering strips 66 are an integral part of the diaper, and remain connected to the diaper after placement about the infant.

Another embodiment of the diaper of the present invention is illustrated in FIG. 8, in which like reference numerals designate like parts. In this embodiment, the tape strip 74 is located intermediate the first and second side sections 44 and 50, respectively, of the diaper side margins 52, and may comprise a double-faced tape strip having adhesive 80 on one surface fixedly attached to an inner surface of the first side margin section 44, and adhesive 82 on an opposed surface of the tape strip 74 releasably attached to an inner release surface 77 of the covering strip 66 which in this embodiment comprises a single ply of the second side section 50 defined by the first and second slits and a slit 84 extending along the diaper side edge 48 in the region of the covering strip 66. In use, the covering strip 66 is peeled from the adhesive 82 on the tape strip 74, and the adhesive 82 facing through the opening 72 of the side margin 52 may be utilized to secure the diaper about the infant while the adhesive 80 retains the tape strip 74 on the first side section 44 of the backing sheet 24.

The foregoing detailed description is given for clearness of understanding only, and no unnecessary limitations should be understood therefrom, as modifications will be obvious to those skilled in the art.

I claim:

1. A disposable diaper, comprising:
an absorbent pad assembly having a pair of side edges, a pair of end edges connecting the side edges, a pair of opposed waistline portions adjacent said end edges and a crotch portion therebetween, an absorbent pad having a side edge spaced inwardly from one of the pad assembly side edges, and a backing sheet of thermoplastic material covering a back surface of said pad and having a doubled side margin extending past the side edge of said pad, said side margin comprising first and second facing sections of the backing sheet extending inwardly from a fold line of the side margin defining the one side edge of the pad assembly, with the first and second sections being fused together in one waistline region adjacent one of the pad assembly end edges, the other side margin being allochirally related to said side margin, said side margins in the one waistline region having a first elongated slit means generally aligned with and spaced inwardly from the fold line of said side margin, and a second slit means extending from the first slit means to the fold line of the side margin, with said first and second slit means defining hinged flaps adjacent the side edges of the pad assembly, said flaps each having a release surface formed by the first and second fused sections; and
a pressure-sensitive tape strip secured to a surface of said side margin and covering said flap, said tape strip having adhesive facing toward the flap, with said flap being releasably attached to said adhesive and being peeled from the tape strip to expose the adhesive for use in securing the diaper about an infant.

2. The diaper of claim 1 wherein the flaps are hinged toward the one end edge of the pad assembly.

3. The diaper of claim 1 wherein the flaps are hinged away from the one end edge of the pad assembly.

4. A disposable diaper, comprising:

an absorbent pad assembly having a pair of side edges, a pair of end edges connecting the side edges, a pair of opposed waistline portions adjacent said end edges and a crotch portion therebetween, an absorbent pad having a side edge spaced inwardly from one of the pad assembly side edges, and a backing sheet of thermoplastic material covering a back surface of said pad and having a doubled side margin extending past the side edge of said pad, said side margin comprising first and second facing sections of the backing sheet extending inwardly from a fold line of the side margin defining the one side edge of the pad assembly, with the first and second sections being fused together in one waistline region adjacent one of the pad assembly end edges, the other side margin being allochirally related to said side margin, said side margins in the one waistline region having first and second spaced slit means extending inwardly from the fold line of said side margin, with said first and second slit means defining hinged flaps adjacent the side edges of the pad assembly, said flaps having a release surface formed by the first and second fused sections and hinging along a line connecting the medial ends of said first and second slit means; and a pressure-sensitive tape strip secured to a surface of said side margin and covering said flap, said tape strip having adhesive facing toward the flap, with said flap being releasably attached to said adhesive and being peeled from the tape strip to expose the adhesive for use in securing the diaper about an infant.

* * * * *